(12) United States Patent
Fridman

(10) Patent No.: US 9,227,059 B2
(45) Date of Patent: *Jan. 5, 2016

(54) METHODS AND APPARATUS FOR COCHLEAR IMPLANT SIGNAL PROCESSING

(71) Applicant: Advanced Bionics AG, Staefa (CH)

(72) Inventor: Gene Y. Fridman, Baltimore, MD (US)

(73) Assignee: Advanced Bionics AG, Staefa (CH)

( * ) Notice: Subject to any disclaimer, the term of this patent is extended or adjusted under 35 U.S.C. 154(b) by 203 days.

This patent is subject to a terminal disclaimer.

(21) Appl. No.: 14/040,660

(22) Filed: Sep. 28, 2013

(65) Prior Publication Data

US 2014/0031899 A1  Jan. 30, 2014

Related U.S. Application Data

(62) Division of application No. 13/050,805, filed on Mar. 17, 2011, now Pat. No. 8,565,890, which is a division of application No. 11/096,402, filed on Apr. 1, 2005, now Pat. No. 7,953,490.

(60) Provisional application No. 60/559,296, filed on Apr. 2, 2004.

(51) Int. Cl.
*A61N 1/08* (2006.01)
*A61N 1/36* (2006.01)
*A61N 1/05* (2006.01)

(52) U.S. Cl.
CPC .......... *A61N 1/36032* (2013.01); *A61N 1/0541* (2013.01)

(58) Field of Classification Search
CPC .................. A61N 1/36032; A61N 1/0541
See application file for complete search history.

(56) References Cited

U.S. PATENT DOCUMENTS 5,271,397 A  12/1993  Seligman et al.

OTHER PUBLICATIONS

Non-Final Office Action received in U.S. Appl. No. 13/050,763 dated Jul. 20, 2012.
Non-Final Office Action received in U.S. Appl. No. 13/050,805 dated Nov. 20, 2012.
Final Office Action received in U.S. Appl. No. 13/050,805 dated Apr. 17, 2013.

*Primary Examiner* — Tammie K Heller
(74) *Attorney, Agent, or Firm* — ALG Intellectual Property, LLC

(57) ABSTRACT

An exemplary speech processor configured to be used in a cochlear implant system includes signal processing circuitry that 1) separates an incoming audio signal into a plurality of channels, wherein each channel included in the plurality of channels includes a channel signal included in a plurality of channel signals and representing a portion of the audio signal, 2) selects one or more channel signals from the plurality of channel signals that have a spectral power that exceeds a predetermined threshold value, the selected one or more channel signals corresponding to one or more channels included in the plurality of channels, and 3) designates only the one or more channels that correspond to the selected one or more channel signals to be used for stimulation representative of the incoming audio signal.

18 Claims, 4 Drawing Sheets

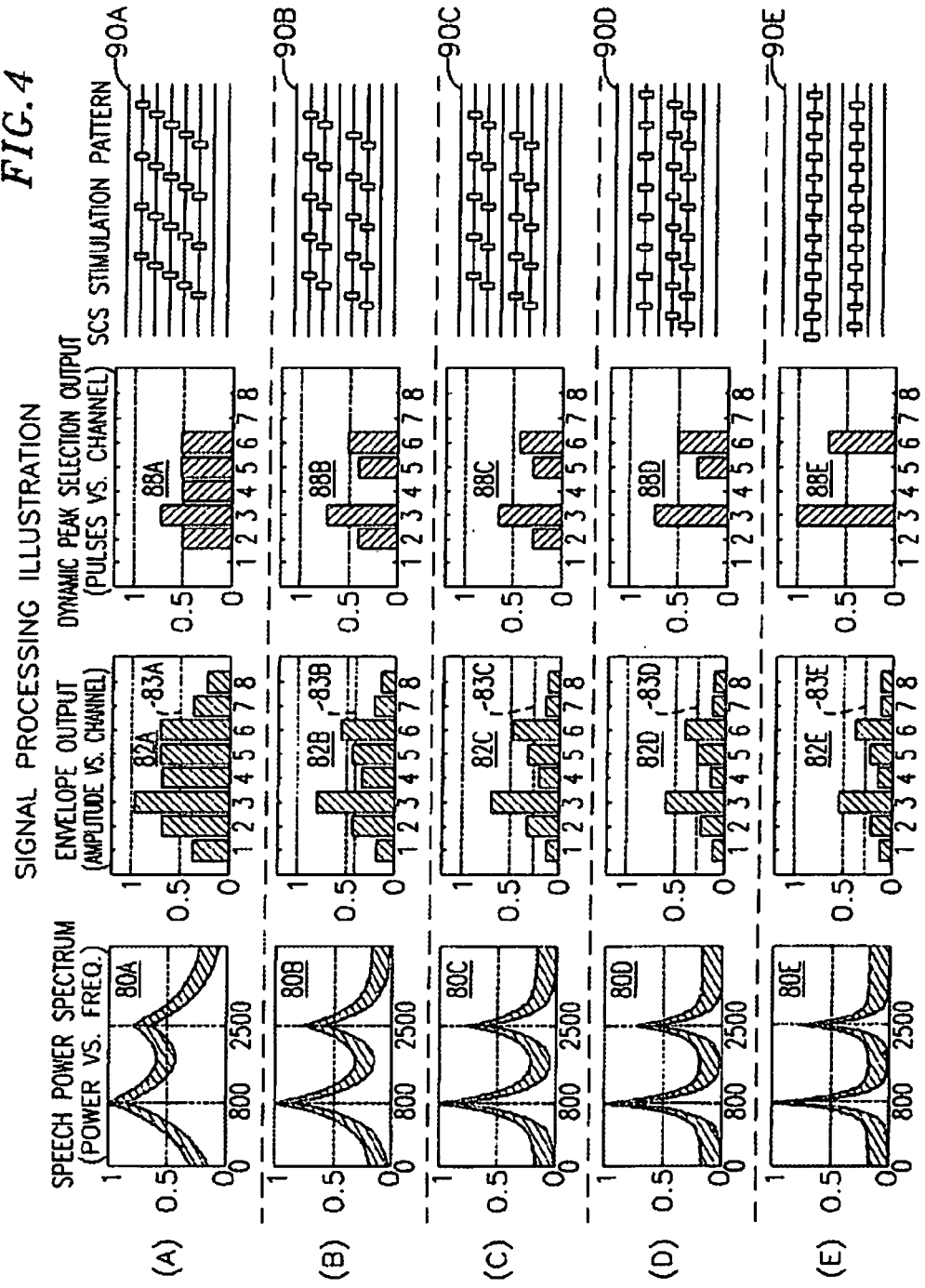

METHODS AND APPARATUS FOR COCHLEAR IMPLANT SIGNAL PROCESSING

RELATED APPLICATIONS

The present application is a divisional application of U.S. patent application Ser. No. 13/050,805, by Gene Y. Fridman, filed Mar. 17, 2011 and issued as U.S. Pat. No. 8,565,890 on Oct. 22, 2013, which is a divisional application of U.S. patent application Ser. No. 11/096,402, by Gene Y. Fridman, filed Apr. 1, 2005, now issued as U.S. Pat. No. 7,953,490, which claims priority under 35 U.S.C. §119(e) to U.S. Provisional Patent Application No. 60/559,296 by Gene Y. Fridman, filed Apr. 2, 2004 and entitled "Methods and Apparatus For Cochlear Implant Signal Processing," the contents of which are hereby incorporated by reference in their entirety.

BACKGROUND INFORMATION

Cochlear implant systems provide the sensation of sound to those who are profoundly deaf. Unfortunately, the clarity of the sound that is perceived is not always as good as desired.

U.S. Pat. No. 5,626,629, and U.S. Pat. No. 5,601,617, both of which patents are incorporated herein by reference, teach or use some speech processing and stimulation strategies that may be used by a cochlear implant system, such as the CLARION or C-II cochlear stimulation systems available from Advanced Bionics Corporation, of Sylmar, Calif. One common speech processing strategy used in the prior art is a simultaneous analog stimulation (SAS) strategy, wherein more than one channel may provide stimulation at the same time. Another common speech processing strategy used and known in the art is continuous interleaved sampling (CIS) strategy. U.S. Pat. No. 6,289,247, also incorporated herein by reference, teaches other types of speech processing and stimulation strategies that may be used by a cochlear implant system. U.S. Pat. No. 5,597,380, and U.S. Pat. No. 5,271,397 are likewise incorporated herein by reference.

SUMMARY

Dynamic selection of the number of channels to stimulate can provide greater sound clarity. Once a selection of the channels to stimulate has been made, stimulation can be removed from the other channels. Stimulation can be applied to the selected channels only, if desired.

In one configuration, the selected channels are the ones on which the spectral power is above the mean of all the available channels. In this example, few channels get stimulated at any one time for a given frame, and the contrast of the stimulation is enhanced. The contrast is improved further because the perceived loudness on the fewer number of channels will increase due to faster presentation rate. Also, the temporal resolution will increase as the number of stimulated channels is decreased.

Further, because the selected channels are the ones on which the spectral power is above a threshold, e.g., above the mean, or above the average, or above some other measure of the spectral power on all of the channels, the selection of channels often is not static. Rather, the selection can be dynamic based on the spectral power in the channels.

One configuration of a stimulation system applies stimulation to the areas of the cochlea which correspond in the desired way to spectral power, such as the selected spectral power. Stimulation may be removed from all other locations along the cochlea corresponding to channels having a low spectral power, for example below the selected spectral power.

Cochlear implants having one or more of the characteristics described above may offer increased speech clarity and higher temporal performance. They may also offer increased speech clarity without consuming excessive power.

The present invention advantageously provides an increase in perceived SNR (signal-to-noise ratio) by removing stimulation from low power channels. Further, the invention provides an increase in spectral contrast since fewer channels receive a higher pulse rate. Additionally, the invention provides an increase in temporal resolution since the integration frame is shorter for a smaller number of channels.

BRIEF DESCRIPTION OF THE DRAWINGS

The above and other aspects of the present inventions will be more apparent from the following more particular description thereof, presented in conjunction with the following drawings wherein:

FIG. 4 depicts an illustration of how the present inventions may process signals to provide stimulation only on those channels of high spectral power.

Corresponding reference characters indicate corresponding components throughout the several views of the drawings.

DETAILED DESCRIPTION

The following description is of the best mode presently contemplated for carrying out one or more aspects of the present inventions. This description is not to be taken in a limiting sense, but is made merely for the purpose of describing the general principles of the invention. The scope of the invention should be determined with reference to the claims.

In one exemplary apparatus and methods, improved speech clarity can be achieved by only stimulating the locations of the cochlea which correspond to high spectral power, namely spectral power above a defined spectral power. Additionally, stimulation can be removed from all other locations along the cochlea with low spectral power, namely spectral power below the selected spectral power. "Low spectral power" and "High spectral power" are defined here as being that spectral power that is below and above the selected spectral power, respectively. In one aspect of the inventions, the selected spectral power is estimated by the signal average. In the examples described herein, the "signal average" is the sum of the channel signals divided by the total number of channels.

A representative cochlear stimulation system with which the present invention may be used is described in U.S. Pat. No. 5,603,726, which patent is incorporated herein by reference. Other cochlear stimulation systems with which the present invention may be used are found in U.S. Pat. Nos. 6,308,101; 6,219,580; and 6,272,382; which patents are also incorporated herein by reference.

Figure 1:
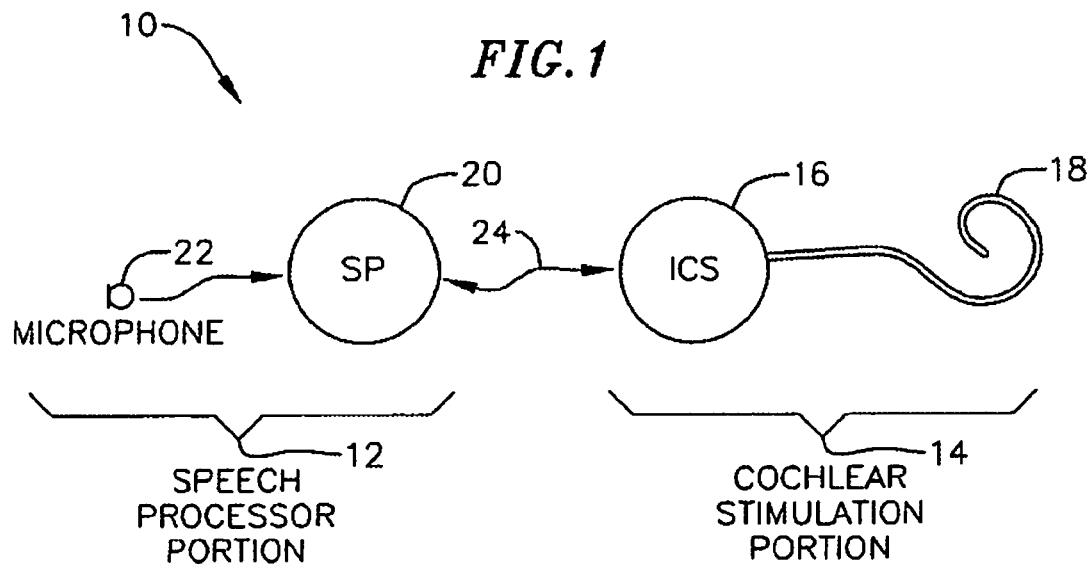
FIG. 1 shows a cochlear stimulation system.

FIG. 1 shows a typical cochlear stimulation system 10 comprising a speech processor portion 12 and a cochlear stimulation portion 14. The cochlear stimulation portion 12 is usually implanted, and includes an implantable cochlear stimulator (ICS) 16 and a cochlear lead 18. The lead 18 includes a multiplicity of electrode contacts thereon (not visible in FIG. 1) through which electrical stimulation pulses, generated by the ICS 16, are applied to selected locations or areas of the cochlea.

The speech processor portion 12 includes a speech processor (SP) 20 and a microphone 22. The microphone 22 may be physically connected to the SP 22, or connected through an appropriate wireless link 21. The microphone 22 senses acoustic sound and transduces it to an electrical signal. The electrical signal from the microphone has different intensities as a function of the loudness of the audio signal that is sensed. The electrical signal from the microphone 22 is then processed by the SP 20 in accordance with a selected speech processing strategy. Based on the type of processing strategy employed, appropriate control signals are generated and sent to the ICS 16 over link 24. The ICS 16 responds to these control signals by generating appropriate stimulation signals that are applied to tissue at various locations along the inside of the cochlea through the electrode contacts located near the distal end of the lead 18.

Typically, the speech processor portion 12 of the cochlear stimulation system 10 is external (not implanted), and the link 24 between the SP 20 and the IPG 16 is a transcutaneous link. However, it is to be understood that parts of the speech processor portion 12 may also be implanted. In a fully-implantable cochlear stimulation system, such as is described in the U.S. Pat. No. 6,308,101, all of the speech processor portion 12 is implanted. When both the SP portion 12 and the cochlear stimulation portion 14 are implanted, the SP 20 and the ICS 16 may reside in respective housings, as shown in FIG. 1, or the circuitry associated with both the SC 20 and the ICS 16 may be combined into a single housing.

Figure 2:
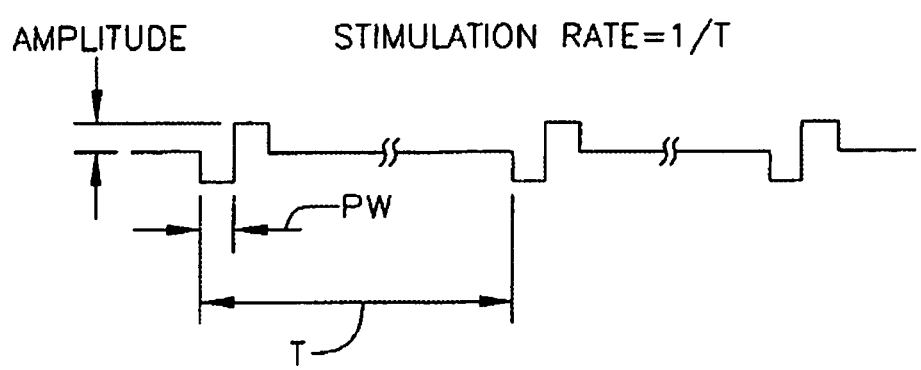
FIG. 2 shows a typical biphasic stimulation waveform generated by an implantable cochlear stimulator (ICS)

A biphasic pulse of the type that is generated by the ICS 16 in response to the control signals received from the SP 20 is shown in FIG. 2. In general, the amplitude and/or pulse width (PW) of the pulses may be varied to adjust the magnitude of the stimulus. Also, the frequency, or stimulation rate, at which the pulses are generated may be controlled, as needed.

A preferred platform for launching the present invention is shown in U.S. Pat. No. 6,219,580, previously incorporated herein by reference. Some features associated with that platform are shown in the signal flow diagram of FIG. 3. Additionally, a schematic of a processor assembly used on the platform is shown in FIG. 3A, showing a physical partitioning of the ICS2 portion of the platform described and illustrated in FIG. 14 of U.S. Pat. No. 6,219,580. The ICS2 consists of electronic circuitry that fits inside a hermetically sealed, U-shaped ceramic case 300, e.g., of the type disclosed in U.S. Pat. No. 4,991,582, incorporated herein by reference. The package design may be the same as is used by the ICS described in the '726 patent, previously referenced. The power and telemetry coils 302, and the back telemetry coil 304, and all circuitry are mounted on a ceramic hybrid 306 inside of the case 300. The majority of the circuitry is integrated into custom integrated circuits (ICs). Two IC's are employed—one analog IC 308 and one digital IC 310. Discrete components are used as necessary, e.g. coupling capacitors Cc. Attachment of the circuitry to the sixteen external electrodes and one indifferent (reference) electrode is through a bulkhead connector 312 at one end of the case. (Note that Electrodes are numbered 1 through 16, with 1 the most apical and 16 the most basal.) Provision for an additional indifferent electrode and two stapedius electrodes are also made in the ICs.

Figure 3:
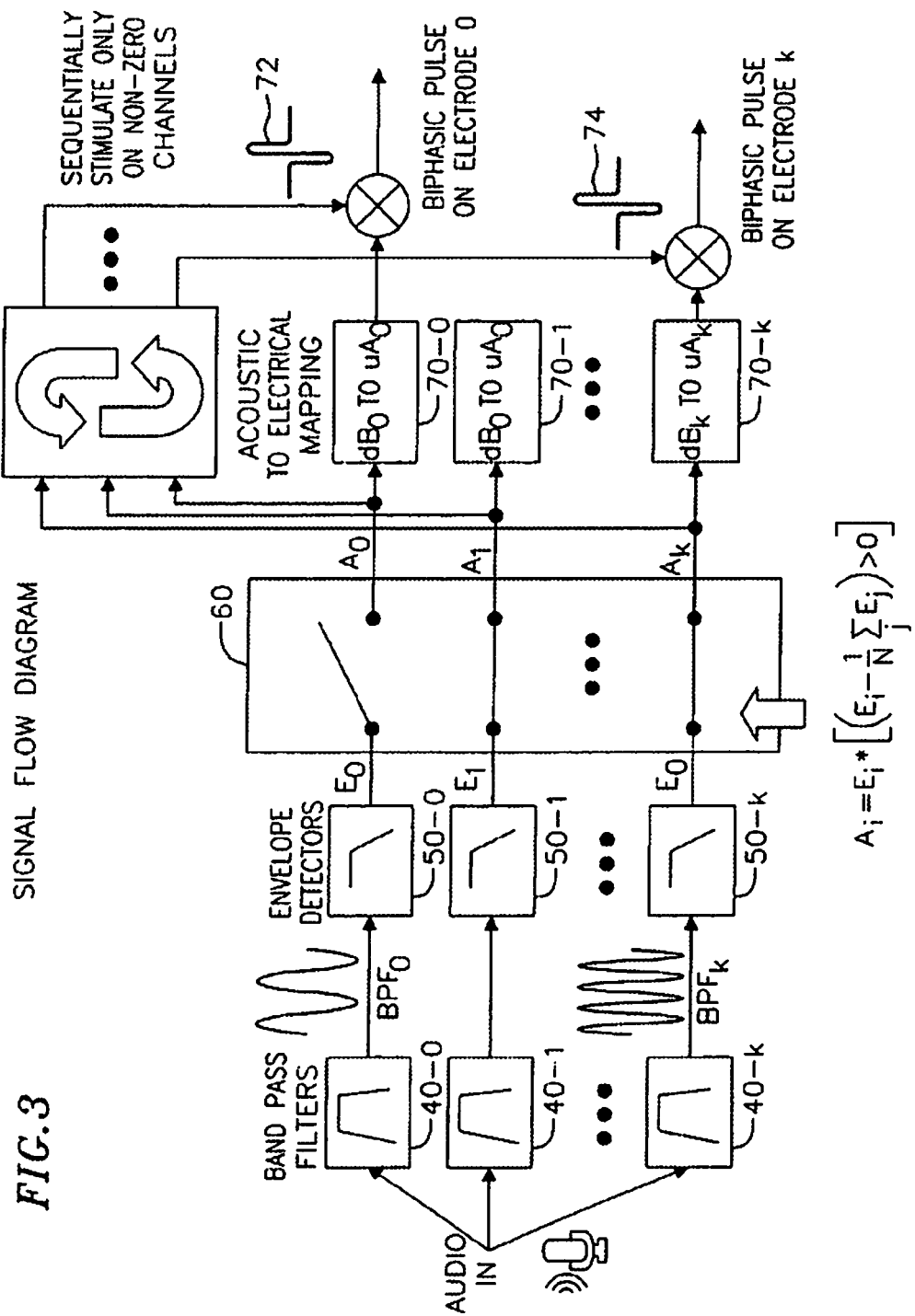
FIG. 3 illustrates the signal flow through a cochlear stimulation system in accordance with the present inventions.
Figure 3A:
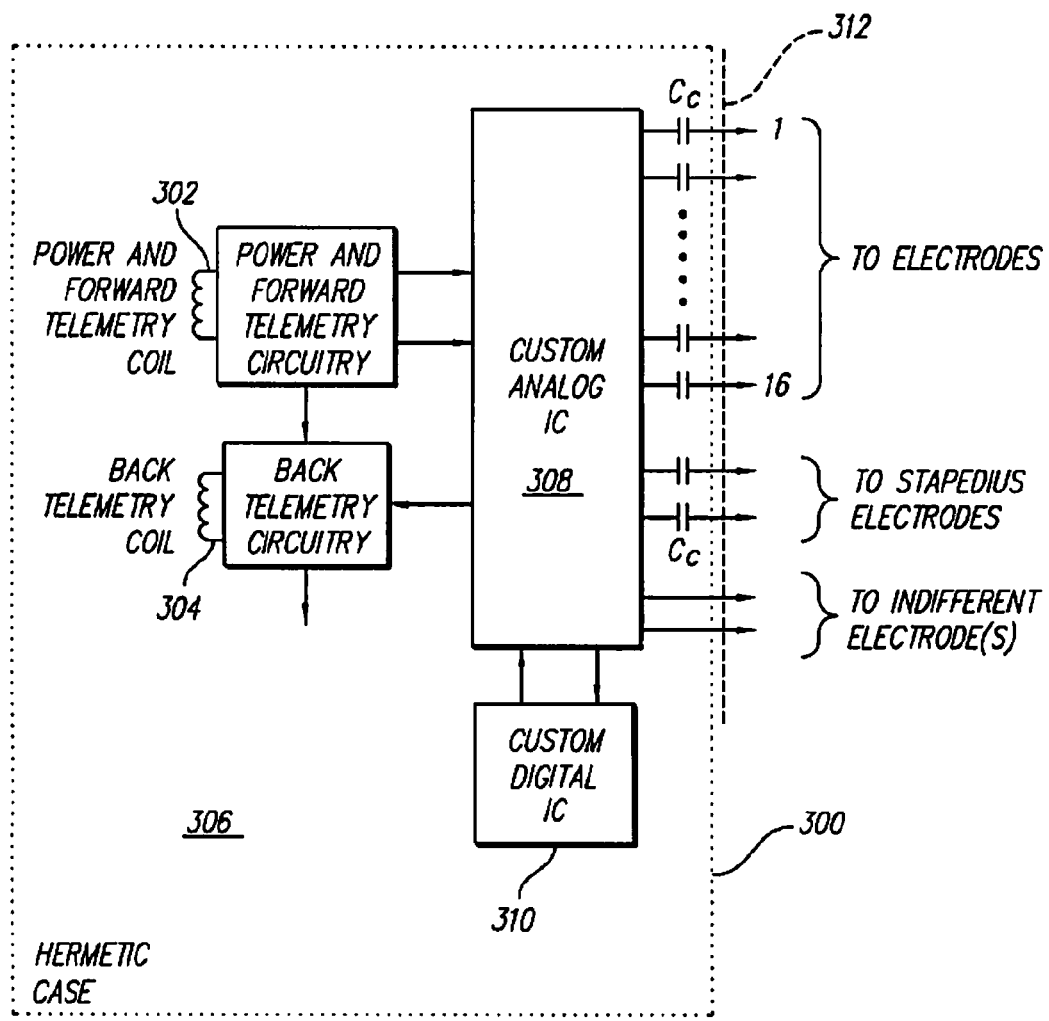
FIG. 3A is a schematic of a processor assembly used on a platform for the stimulation system.

As seen in FIG. 3, the signal generated by the microphone 22 is split into frequency bands by a bank of bandpass filters 40-0, 40-1, . . . 40-k connected in parallel. Each bandpass filter 40 receives the microphone signal. Each bandpass filter 40 has a center frequency that allows signal frequencies within a specified band to pass therethrough. The bandpass filter 40-0, for example, allows relatively low frequency signals to pass through. The bandpass filter 40-k, on the other hand, allows only high frequency signals to pass through. The bank of bandpass filters is an example of apparatus that can divide an incoming audio signal into channels.

The signals in each frequency band are then subjected to envelope detectors 50-0, 50-1 . . . 50-k. Each of these envelope detectors 50 senses the spectral power component of the signal in its respective frequency band. This spectral power component is represented in FIG. 3 as the signals $E_0, E_1, \ldots E_K$. The average of these signals $E_0, E_1, \ldots E_K$ is dynamically determined. The average of the power of the spectral channels can be determined through appropriate processing carried out on the ICS2 (FIG. 3A). This average allows selection of a selected spectral power, which can then be used to select which of the signals $E_0, E_1, \ldots E_K$ represents "low" spectral power, and which of the signals represents "high" spectral power. The envelope detector is an example of apparatus that can determine the spectral power of a signal. The selected spectral power is an example of a threshold that can be used to differentiate between high and low spectral power signals, and the threshold can be determined through appropriate processing carried out on the ICS2 (FIG. 3A). A selector circuit 60 allows only those signals having "high" spectral power to be sent on to the ICS for stimulus generation. The channels having "low" spectral power are de-selected, i.e., removed so that stimulation pulses corresponding to the channels having "low" spectral power is effectively turned off. These low spectral power channels will be effectively zero channels, because they will be turned off, or those channels will be set at zero or have no pulses applied for those channels. The selector circuit 60 is an example of an apparatus for selecting channels having spectral power above a threshold value. The selector circuit can be implemented in the ICS2 (FIG. 3A).

Further, the signals of "high" spectral power that pass through the selector circuit 60 are sequenced using sequencer 64 so that the stimuli generated by the ICS 16 are applied sequentially only on the non-zero (spectral power) channels. Acoustic-to-electrical mapping of the signals is further carried out with mapping circuits 70-0, 70-1, . . . 70-k, which mapping further conditions the signals that are applied to the electrodes on the lead 18. A biphasic stimulus pulse is then applied on the non-zero channels in sequence as controlled by the sequencer 64 and as conditioned by appropriate mapping circuits 70. The mapping circuits are an example of an apparatus for sequentially applying electrical stimuli only to the electrodes of channels having a spectral power above a threshold value.

Because the spectral power in each channel changes dynamically as a function of the acoustic signals sensed through the microphone 22, the non-zero channels through which a stimulus, or stimuli, are applied also changes dynamically. However, for any cycle of the sequencer 64, there will be some zero channels on which no stimulus will be provided, and some non-zero channels on which a biphasic stimulus pulse is applied. The biphasic stimulus provides a loudness associated with the various parameters of the stimulation pulse train, such as the amplitude, pulse width of the pulses, and the time between pulses. —We refer to the perceived loudness on a given channel as intensity. Intensity is controlled by the spectral power of that channel. The intensity in some applications will be the combination of the amplitude and the pulse width and number of pulses per unit time, but it should be understood that intensity for purposes of the present discussion may be manifested in other ways, for example amplitude only with relatively constant pulse width, or pulse width with relatively constant amplitude. For the example illustrated in FIG. 3, the spectral power is non-zero only in the 0th channel and the kth channel. All of the other channels are zero. Thus, a biphasic pulse 72 is applied to electrode 0 on lead 18, and a biphasic pulse 74 is applied to electrode k on the lead 18. Electrode 0, corresponding to channel 0, which represents the channel having the lowest frequency components, is located distally near the end of the lead 18 so that when the lead is inserted into the cochlea this electrode 0 is close to those nerve cells deep in the cochlea that recognize lower frequency signals. Electrode k, corresponding to channel k, which represents a channel having higher frequency components, is located more proximally on the lead 18 so that when the lead is inserted into the cochlea this electrode k is close to those nerve cells closer to the entrance of the cochlea that recognize higher frequency signals.

The operation of the invention is depicted in signal processing illustration of FIG. 4. Note that FIG. 4 is divided into five rows, labeled (A), (B), (C), (D), and (E). Each row represents a different example of a signal processing condition.

In row (A) of FIG. 4, the speech power spectrum has peaks at about 800 and 2500 Hz, as seen in the Speech Power Spectrum graph 80A. However, these peaks are not sharp peaks, meaning that the spectral power is spread over many of the channels. This creates a power spectral spread in each of eight channels as illustrated in "Envelope Output" chart 82A. This is basically a chart of the signals $E_0, E_1, \ldots E_K$, (see FIG. 3), where k=8 in this example. The average of these signals $E_0, E_1, \ldots E_K$ is determined and is used as a threshold. The average is taken as equal to Sum(Ej)/K, where Sum is the conventional sum of elements (Ej), "j" is the channel number, and "K" is the total number of channels, or "k" in this example, where k=8. This threshold, or "threshold value" 83A, is then used as the selected spectral power, and used to identify those channels above the threshold value and those channels below the threshold value. For the example of this row (A), five of the eight channels—channels 2, 3, 4, 5 and 6—have spectral power signals above the threshold 83A. Hence, these five channels are selected, as seen in the Dynamic Peak Selection Output chart 88A, and biphasic pulses are applied sequentially to these five channels, as illustrated in the Stimulation Pattern chart 90A.

The speech power spectrum in rows (B), (C), (D) and (E) of FIG. 4 shows that the spectral peaks, all of which are at approximately 800 and 2500 Hz, become increasingly sharper. Thus, for example, in Row (E), only two of the eight channels—channels 3 and 6—have spectral power above the average 83E. Hence, only these two channels are selected, as seen in the Dynamic Peak Selection Output chart 88(E), and biphasic pulses are applied sequentially to just these two channels, as illustrated in the Stimulation Pattern chart 90(E). Note also the rate at which the pulses are applied to these two channels is faster than the rate would be if more channels were selected. This increases the temporal resolution for the stimulated channels since the time between stimuli is shorter. Thus, in general, the temporal resolution increases since the integration frame is shorter for a smaller numbers of channels.

Thus, it is seen that in operation for one aspect of the present signal processing method, the speech processing strategy operates by splitting the incoming signal (obtained from the microphone 22, or equivalent) into k frequency bands or channels. The spectral power component of the signal present in each frequency band is determined. The average (or mean, or other suitable collective measure) of these spectral power components, $E_0, E_1, \ldots E_K$, is determined and is used as a threshold value. Only those channels having a spectral power component above the threshold value is selected for stimulation as a non-zero channel. The other channels are de-selected, as zero spectral power channels, and no stimulus is applied on these zero channels. The stimuli are then applied sequentially only on the selected channels.

While the mean is one example of a criterion for identifying a selected spectral power to use, for example as a threshold value, other criteria may be used as well. Other examples include other statistical methods, such as using variance to determine a threshold value or a combination of the average and variance to determine a threshold value. Other examples include using a weighted average, such as where the weight may be dynamically assigned or where it is assigned as a function of known speech spectra. Dynamic assignment of a weighting factor may include weighting based on relative or absolute amplitude, based on noise level as may be determined dynamically, for example, or other weighting methods. Additionally, weighting may be applied to incoming signals before they are analyzed or they may be applied to the threshold value or other determinant before calculating which channels will be non-zero and which will be assigned zero values. Other examples for identifying a spectral power to use include identification of the median, or identification of the median with a weight factor applied. Therefore, identification of the selected spectral power may be considered to be based on some function, $f(E_0, E_1, E_2, E_3, \ldots E_K)$, hereafter f(E), as desired, which function is then used to select the non-zero channels. The function may also be a function of time, which will be designated as f(Et), indicating that the function is based preferably on both the spectral power but also on time "t". The function f(E) will be used when indicating that the spectral power is based on the channel energies regardless of any dependence on time.

The function f(Et) can be used or applied dynamically, as a function of on-going speech patterns, and need not be static for a given time period or static for a given user. For example, the mean in the example discussed herein can be determined for the channels on a frame-by-frame basis or on some other basis selected by the designer or technician. The mean (or other criterion) can be determined at regular intervals, or when a selected event occurs, such as when signal levels rise or fall beyond a set level. For present purposes, using a function to select a selected spectral power, different than a previously selected spectral power, more than once during the lifetime of the device will be considered dynamically determining the selected spectral power. Therefore, "t" in f(Et) can be as large as the device lifetime, and as small as a frame or less. Additionally, the number of channels selected for stimulation can be varied. The selection criteria may be the same as described herein, for example, and such selection will allow the number of channels that are stimulated to be changed as a function of time as well. Therefore, the number of channels for stimulation may be selected. At a later time, one or more channel signals may be evaluated, such as by applying a suitable function to the spectral power values for the channel (or each channel desired), and thereafter identifying those channels with spectral power values that exceed a selected value. The number of channels may then be increased or decreased as desired. The number of channels may be decreased or increased dynamically based on the desired criteria or criterion.

Advantageously, the present apparatus and methods can be used to increase the perceived signal-to-noise ratio (SNR)

because the stimulation from the low spectral power channels can be identified and removed. Moreover, the spectral contrast increases since fewer channels receive a higher pulse rate. Additionally, the temporal resolution increases since the integration frame can be made shorter for smaller number of channels. As a further advantage, the power consumption of the cochlear stimulation system can be less than when using simultaneous speech processing strategies, such as SAS.

Because the present invention may operate using less power than an SAS strategy, SAS users who choose the present strategy would have the option of using a behind-the-ear (BTE) speech processor, which consumes less power than the body-worn speech processors.

While the invention herein disclosed has been described by means of specific embodiments and applications thereof, numerous modifications and variations could be made thereto by those skilled in the art without departing from the scope of the invention set forth in the claims.

What is claimed is:

1. A speech processor configured to be used in a cochlear implant system and comprising:
    signal processing circuitry configured to
        separate an incoming audio signal into a plurality of channels, wherein each channel included in the plurality of channels includes a channel signal included in a plurality of channel signals and representing a portion of the audio signal;
        select one or more channel signals from the plurality of channel signals that have a spectral power that exceeds a predetermined threshold value, the selected one or more channel signals corresponding to one or more channels included in the plurality of channels, and
        designate only the one or more channels that correspond to the selected one or more channel signals to be used for stimulation representative of the incoming audio signal.

2. The speech processor of claim 1, wherein the signal processing circuitry is configured to apply a function f(E) to the plurality of channel signals to determine the threshold value for the plurality of channel signals.

3. The speech processor of claim 2, wherein the signal processing circuitry is configured to apply the function by determining a mean of spectral power of at least two channel signals included in the plurality of channel signals and designating the mean as the threshold value.

4. The speech processor of claim 2, wherein the signal processing circuitry is configured to apply the function dynamically.

5. The speech processor of claim 2, wherein the function comprises a spectral power function that determines how much spectral power is present in each of the plurality of channel signals.

6. The speech processor of claim 5, wherein the spectral power function also applies a weight factor.

7. The speech processor of claim 2, wherein the function comprises a spectral power function that is also a function of time, f(Et), where f(Et) indicates that the function is based on both spectral power and on time.

8. A cochlear implant system adapted to receive an incoming audio signal and apply an electrical stimulus to cochlea tissue as a function of spectral and temporal characteristics of the incoming audio signal, the cochlear implant system comprising:
    a signal processing apparatus; and
    a plurality of electrodes adapted to be inserted into cochlea tissue;
    wherein the signal processing apparatus comprises
        circuitry configured to form a plurality of channels connected in parallel, each channel being adapted to receive a portion of the incoming audio signal, the incoming audio signal being divided among the plurality of channels as a function of frequency, wherein each channel of the plurality of channels has a frequency band associated therewith, and wherein each channel produces a respective channel signal having spectral characteristics associated with components of the incoming audio signal that are within the frequency band of that channel, and
        circuitry configured to implement a speech processing strategy that selects how many and which channels within the plurality of channels are used to apply electrical stimuli to cochlea tissue through the plurality of electrodes associated with the selected channels, wherein the speech processing strategy increases or decreases the number of selected channels that apply electrical stimuli as a function of whether the channel signal in at least one of the channels meets a prescribed spectral characteristic;
    wherein each electrode included in the plurality of electrodes is coupled to at least one of the plurality of channels, wherein an electrical stimulus is applied through one of the plurality of electrodes when the channel signal associated with at least one of the channels coupled to the electrode exhibits a spectral characteristic that meets a prescribed spectral characteristic.

9. The cochlear implant system of claim 8, wherein the prescribed spectral characteristic comprises a mean of the spectral power in all channels.

10. The cochlear implant system of claim 8, wherein the prescribed spectral characteristic comprises an average of the spectral power in all channels.

11. The cochlear implant system of claim 8, wherein the speech processing apparatus includes:
    a detector circuit associated with each channel and that is configured to detect whether the spectral power in that channel is "high" or "low", wherein the "high" spectral power comprises power above a set spectral power threshold, and wherein the "low" spectral power comprises spectral power below the set spectral power threshold;
    a selector circuit configured to select the channels having high spectral power and deselects the channels having low spectral power;
    wherein the channels having low spectral power are effectively turned off.

12. The cochlear implant system of claim 11, wherein:
    each detector circuit is configured to sense a spectral power component of the channel signal in its respective frequency band; and
    the set spectral power threshold comprises an average of the spectral power component of all of the channels.

13. The cochlear implant system of claim 11, wherein:
    each detector circuit is configured to sense a spectral power component of the channel signal in its respective frequency band; and
    the set spectral power threshold comprises a mean of the spectral power component of all of the channels.

14. The cochlear implant system of claim 11, further including a sequencer circuit configured to process channel signals having the "high" spectral power sequentially, wherein electrical stimuli are applied to cochlea tissue in a sequence corresponding to the sequence of processing of channel signals having the "high" spectral power.

15. The cochlear implant system of claim 14, further including a mapping circuit adapted to condition the sequentially processed channel signals having the "high" spectral power so that the electrical stimuli applied through the plurality of electrodes produces increased speech clarity and temporal performance for a user of the speech processing apparatus.

16. The cochlear implant system of claim 14, wherein the set spectral power threshold is derived from a frequent measure of the spectral power in all of the plurality of channels, and further wherein the detector circuit is configured to frequently update its determination of whether the spectral power associated with a channel signal in any of the plurality of channels comprises "high" or "low" spectral power, whereby the number of channels through which electrical stimuli is applied to cochlear tissue dynamically changes as the spectral power threshold is updated.

17. The cochlear implant system of claim 16, wherein:
   each detector circuit is configured to sense a spectral power component of the channel signal in its respective frequency band; and
   the set spectral power threshold comprises an average of the spectral power component of all of the channels.

18. The cochlear implant system of claim 16, wherein:
   each detector circuit is configured to sense a spectral power component of the channel signal in its respective frequency band; and
   the set spectral power threshold comprises a mean of the spectral power component of all of the channels.

* * * * *